US00PP29024P2

(12) United States Plant Patent
van Langen

(10) Patent No.: US PP29,024 P2
(45) Date of Patent: Feb. 27, 2018

(54) ***ALOE* PLANT NAMED 'AMIAL1620'**

(50) Latin Name: *Aloe aristata*
Varietal Denomination: AMIAL1620

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 15/530,590

(22) Filed: Feb. 3, 2017

(51) Int. Cl.
*A01H 5/12* (2006.01)

(52) U.S. Cl.
USPC ..... Plt./373

(58) Field of Classification Search
USPC ..... Plt./373, 372
CPC ..... A01H 5/12; A01H 5/02; A01H 5/00
See application file for complete search history.

*Primary Examiner* — Kent L Bell
(74) *Attorney, Agent, or Firm* — Samuel R. McCoy, Jr.

(57) ABSTRACT

A new and distinct *Aloe aristata* cultivar named 'AMIAL1620' which is characterized by a flattened globular profile with foliage arranged in a short, compact rosette. The short, broad foliage is dark green where exposed to ultraviolet light and yellow green where not directly exposed to light, and is densely covered with prominent papillae. Papillae on the abaxial leaf surface are arranged in distinct transverse rows with those papilla along the mibrid bearing spines. The new variety has shown to be uniform and stable in the resulting generations from asexual propagation.

4 Drawing Sheets

Latin name of the genus and species: The Latin name of the genus and species of the novel variety disclosed herein is *Aloe aristata.*

Variety denomination: The inventive variety of *Aloe* disclosed herein has been given the variety denomination 'AMIAL1620'.

BACKGROUND OF THE INVENTION

Parentage: 'AMIAL1620' originated as a naturally occurring, whole-plant mutation of the species *Aloe aristata* (not a named variety or cultivar unpatented). In Spring of 2016 the inventor discovered the mutation at a commercial greenhouse in Heerhugowaard, The Netherlands, growing amongst a crop of the species *Aloe aristata*. The mutation was noted for its short, compact growth habit and prominent white papillae and was subsequently isolated for further evaluation in order to confirm the distinctness and stability of the characteristics first observed. Upon confirmation of distinctness and stability, 'AMIAL1620' was selected for commercialization in the summer of 2016.

Asexual Reproduction: Asexual reproduction of the new cultivar 'AMIAL1620', by way of rooting leaf cuttings, was first initiated in the summer of 2016 at the inventor's commercial greenhouse in Heerhugowaard, The Netherlands. The claimed plant has since been asexually propagated by way of meristematic tissue culture propagation. Through two subsequent generations, the unique features of this cultivar have proven to be stable and true to type.

SUMMARY OF THE INVENTION

The cultivar 'AMIAL1620' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIAL1620'. These characteristics in combination distinguish 'AMIAL1620' as a new and distinct *Aloe aristata* cultivar:

1. 'AMIAL1620' exhibits a flattened globular profile with foliage arranged in a short, compact rosette; and
2. 'AMIAL1620' exhibits short, broad foliage; and
3. 'AMIAL1620' exhibits foliage that is dark green foliage where exposed to ultraviolet light and yellow green where not directly exposed to light; and
4. 'AMIAL1620' exhibits foliage that is densely covered with prominent papillae on both the adaxial and abaxial surfaces; and
5. 'AMIAL1620' exhibits papillae on the abaxial leaf surface which are arranged in distinct transverse rows, and bearing spines in a distinct longitudinal row along the midrib.

BOTANICAL DESCRIPTION OF THE PLANT

Figure 1:
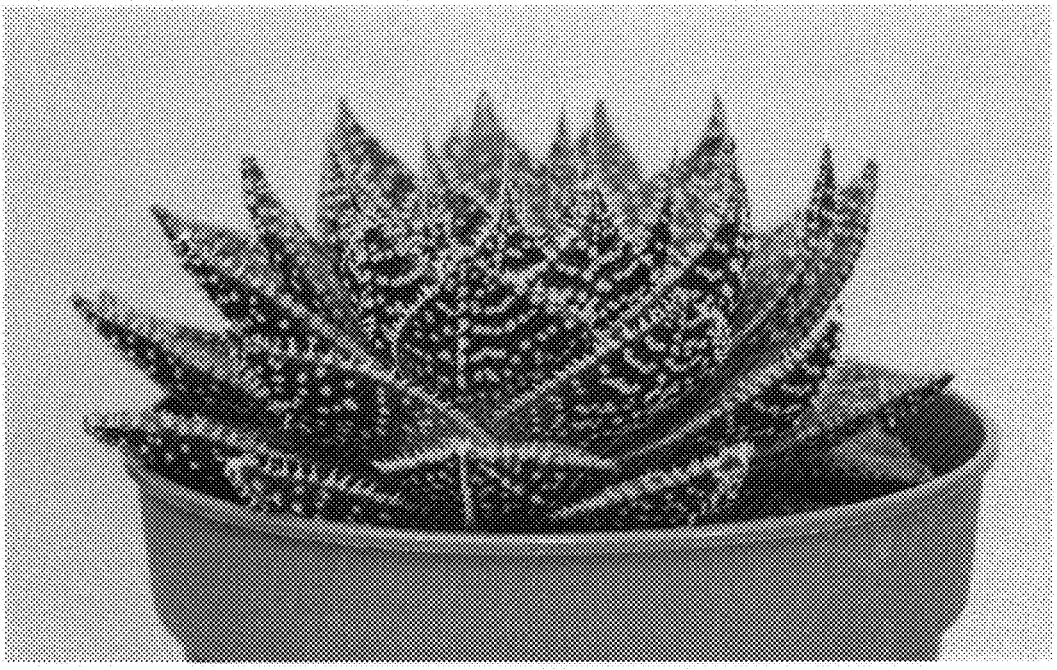
FIG. 1 illustrates, as nearly true as it is reasonably possible to make the same in color photographs of this type, an exemplary plant of 'AMIAL1620' grown in a commercial greenhouse in Heerhugowaard, The Netherlands. This plant is approximately 9 months old, shown planted in a 12 cm container.
Figure 2:
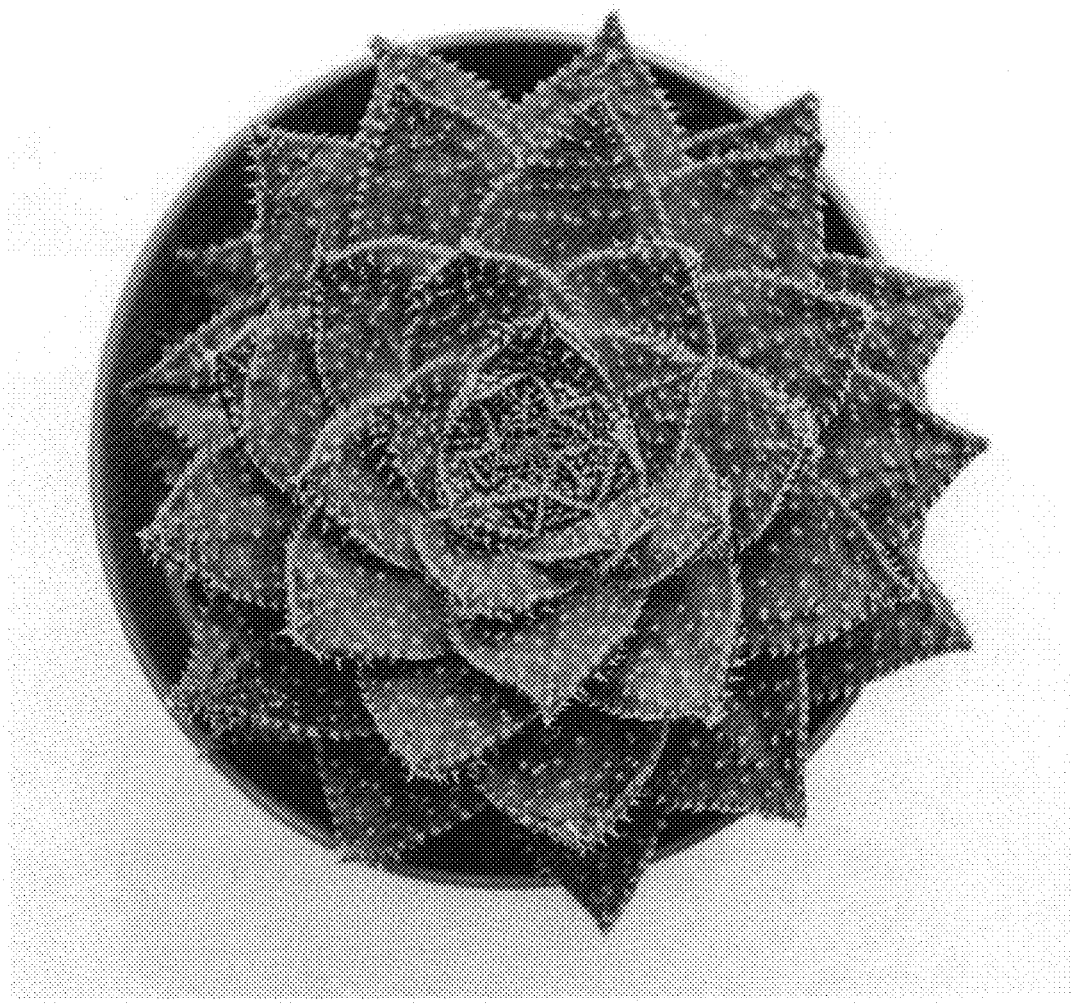
FIG. 2 illustrates, as nearly true as it is reasonably possible to make the same in color photographs of this type, the typical foliage arrangement of 'AMIAL1620'.
Figure 3:
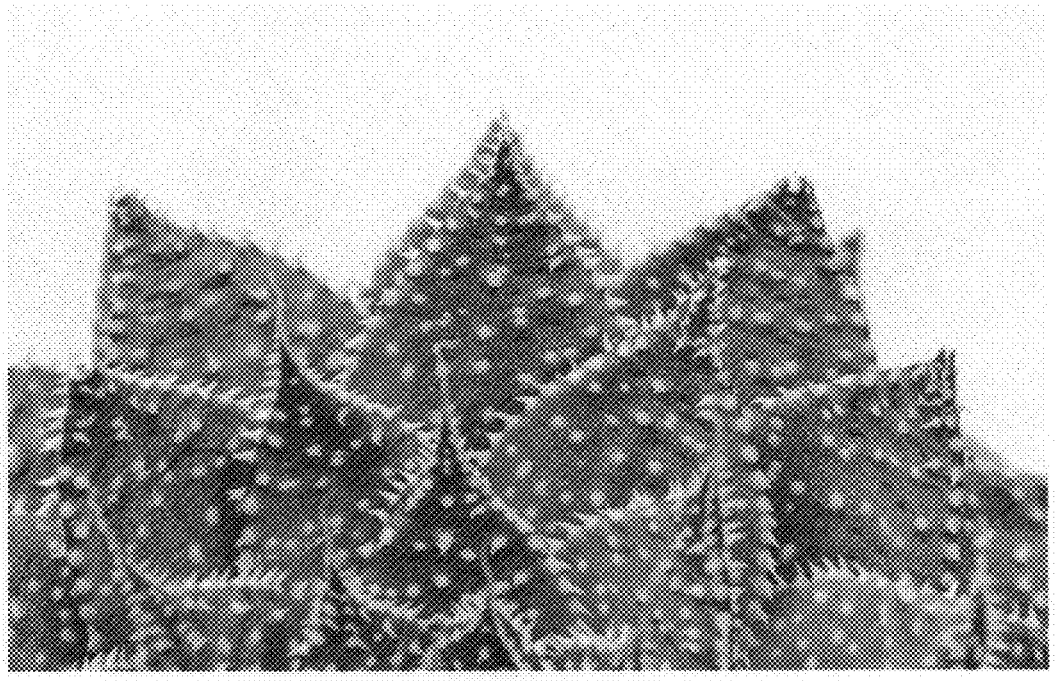
FIG. 3 illustrates, as nearly true as it is reasonably possible to make the same in color photographs of this type, the adaxial surface of the mature foliage 'AMIAL1620'.
Figure 4:
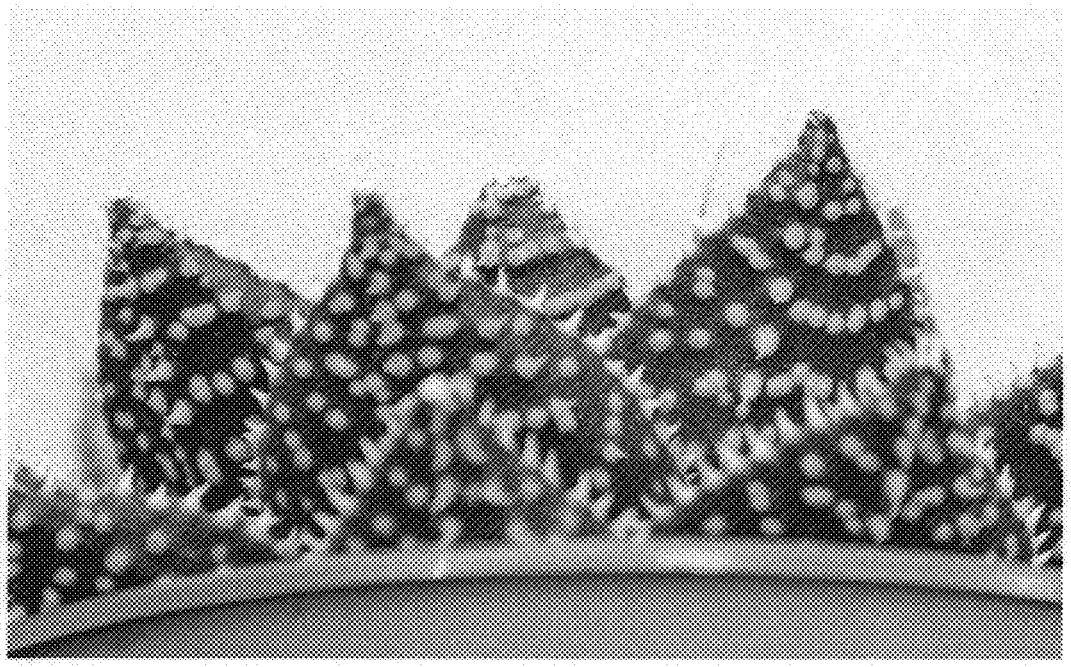
FIG. 4 illustrates, as nearly true as it is reasonably possible to make the same in color photographs of this type, the abaxial surface of the mature foliage 'AMIAL1620'.

The following observations and measurements made in January of 2017 describe averages from a sample set of six specimens of 9 months old 'AMIAL1620' plants grown in 11 cm nursery containers at commercial greenhouse in Heerhugowaard, The Netherlands. Plants were produced using conventional greenhouse production protocols for *Aloe* which consisted of minimal irrigation and fertilizer applications, and chemical pest and disease control measures against mealy bug, *Botrytis* and *Fusarium* as required. Plants were grown under approximately 50 percent shade and no photoperiodic treatments or artificial light was given to the plants.

Those skilled in the art will appreciate that certain characteristics will vary with older or, conversely, with younger plants. 'AMIAL1620' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIAL1620' and a comparison with the parent and closest known comparator, *Aloe aristata*, is provided below.

Plant description:

*Growth habit*.—Succulent perennial with foliage growing in a non-branched basal rosette.

*Plant shape*.—Flattened globular.

*Height from soil level to top of foliar plane*.—7.6 cm.

*Plant spread*.—Average of 12.6 cm.

*Growth rate*.—Low to moderate.

*Plant vigor*.—Low to moderate.

*Propagation*.—Type — Leaf cuttings and meristematic tissue culture. Time to initiate rooting — Approximately 25 days at 18 degrees Celsius. Crop time — Approximately 18 to 22 weeks to produce a marketable plant in a 7 cm container.

*Disease and pest resistance or susceptibility*.—Neither resistance nor susceptibility to typical *Aloe aristata* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 50 leaves per rosette.

*Shape*.—Thick, succulent leaves; obovate in shape.

*Dimensions*.—5.9 cm long, 3.2 cm wide, and 1.1 cm thick, on average.

*Aspect*.—Slightly convex.

*Attitude*.—Slightly curved upward.

*Apex*.—Apiculate; occasionally with a mucronulate tip.

*Base*.—Broad cuneate.

*Margin*.—Dentate; not undulated or lobed.

*Texture, adaxial surface*.—Glabrous and moderately covered with papillae, each approximately 1.0 mm high and 1.0 mm in diameter; papilla bearing spines near margins and apex.

*Texture, abaxial surface*.—Glabrous and densely covered with prominent papillae, more or less arranged in axial rows; each papilla approximately 1.0 mm high and 1.0 mm in diameter; papilla bearing spines near margins, apex, and in a distinct longitudinal row along the midrib.

*Luster, adaxial surface*.—Slightly to moderately glossy.

*Luster, abaxial surface*.—Slightly glossy.

*Color*.—Juvenile foliage, adaxial surface — Green, in between RHS NN137A and 139A, and fading to yellow-green towards the base, nearest to a combination of RHS 144B and 146D; papillae are greyed-green, nearest to RHS 190D. Juvenile foliage, abaxial surface — Green, in between RHS NN137A and 139A, and fading to yellow-green towards the base, nearest to a combination of RHS 144B and 144C; papillae are greyed-green, in between RHS 191B and 191C. Mature foliage, adaxial surface — In between yellow-green, nearest to RHS 147A, and greyed-green, nearest to RHS N189A but darker; darker towards the base, nearest to a combination of RHS 137A, 192C and 192D; papillae are greyed-green, RHS 190A. Mature foliage, abaxial surface — Yellow-green, RHS 147A but darker; fading lighter towards the base, nearest to a combination of RHS 146D, 192C, and 197C; papillae are colored in between green-white, RHS 157D, and greyed-green, RHS 191D.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'AMIAL1620' differ from the parent an unnamed, unpatented plant of, *Aloe aristata*, which is also the closest known comparator, in the following characteristics described in Table 1 below.

TABLE 1

| Characteristic | 'AMIAL1620' | Unnamed, unpatented plant of *Aloe aristata* |
|---|---|---|
| Plant height. | Shorter than the parent. | Taller than 'AMIAL1620'. |
| Leaf size. | Leaves are broader and shorter than those of the parent. | Leaves are longer and narrower than those of 'AMIAL1620'. |
| General coloration of mature foliage. | Dark green. | Green to yellow green and suffused with greyed-green. |
| Leaf papillae. | Large prominent papilla that are white in color; arranged in rows on the abaxial leaf surface. | Papillae are smaller, less prominent, and not as white as those of 'AMIAL1620'. |

That which is claimed is:

1. A new and distinct variety of *Aloe aristata* plant named 'AMIAL1620', substantially as described and illustrated herein.

* * * * *